US008637430B2

(12) United States Patent
Arora et al.

(10) Patent No.: US 8,637,430 B2
(45) Date of Patent: *Jan. 28, 2014

(54) WEB SUBSTRATE HAVING ACTIVATED COLOR REGIONS IN TOPICAL ADDITIVE REGIONS

(75) Inventors: Kelyn Anne Arora, Cincinnati, OH (US); John Lee Hammons, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 601 days.

This patent is subject to a terminal disclaimer.

(21) Appl. No.: 12/766,705

(22) Filed: Apr. 23, 2010

(65) Prior Publication Data

US 2011/0264065 A1   Oct. 27, 2011

(51) Int. Cl.
*B41M 1/26* (2006.01)
*B41M 5/34* (2006.01)

(52) U.S. Cl.
USPC ............ 503/204; 430/200; 503/201; 503/206

(58) Field of Classification Search
USPC ................................................ 503/200–226
See application file for complete search history.

(56) References Cited

U.S. PATENT DOCUMENTS

| 3,414,459 A | 12/1968 | Wells |
| 3,547,723 A | 12/1970 | Gresham |
| 3,556,907 A | 1/1971 | Nystrand |
| 3,708,366 A | 1/1973 | Donnelly |
| 3,738,905 A | 6/1973 | Thomas |
| 3,867,225 A | 2/1975 | Nystrand |
| 4,438,167 A | 3/1984 | Schwarz |
| 4,483,728 A | 11/1984 | Bauernfeind |
| 4,705,742 A | 11/1987 | Lewis |
| 4,808,086 A | 2/1989 | Evans et al. |
| 4,826,550 A | 5/1989 | Shimizu et al. |
| 4,834,741 A | 5/1989 | Sabee |
| 4,968,313 A | 11/1990 | Sabee |
| 5,094,761 A | 3/1992 | Trinh et al. |
| 5,143,679 A | 9/1992 | Weber |
| 5,156,793 A | 10/1992 | Buell et al. |
| 5,167,897 A | 12/1992 | Weber et al. |
| 5,197,958 A | 3/1993 | Howell |
| 5,202,173 A | 4/1993 | Wu et al. |
| 5,246,433 A | 9/1993 | Hasse |
| 5,254,111 A | 10/1993 | Cancio et al. |
| 5,296,184 A | 3/1994 | Wu et al. |

(Continued)

FOREIGN PATENT DOCUMENTS

| EP | 0934737 A1 | 8/1999 |
| EP | 1591131 A1 | 11/2005 |

(Continued)

OTHER PUBLICATIONS

International Search Report dated Apr. 14, 2011, 5 pages.

(Continued)

*Primary Examiner* — Bruce H Hess
(74) *Attorney, Agent, or Firm* — Melody A. Jones

(57) ABSTRACT

The present invention relates to a web substrate comprising an activatable colorant and at least one region comprising a topical additive. A first activated color region is produced in the web substrate upon exposure to a first external stimulus and a second activated color region is produced within the first activated color region upon exposure to a second external stimulus. The second activated color region coincides with the topical additive region.

20 Claims, 7 Drawing Sheets

(56) References Cited

U.S. PATENT DOCUMENTS

| | | | |
|---|---|---|---|
| 5,338,504 A | 8/1994 | Wang et al. |
| 5,354,597 A | 10/1994 | Capik et al. |
| 5,464,401 A | 11/1995 | Hasse |
| 5,468,323 A | 11/1995 | McNeil |
| 5,503,076 A | 4/1996 | Yeo |
| 5,518,801 A | 5/1996 | Chappell et al. |
| 5,527,304 A | 6/1996 | Buell |
| 5,575,783 A | 11/1996 | Clear |
| 5,591,155 A | 1/1997 | Nishikawa |
| 5,607,760 A | 3/1997 | Roe |
| 5,628,097 A | 5/1997 | Benson et al. |
| 5,628,741 A | 5/1997 | Buell |
| 5,643,588 A | 7/1997 | Roe et al. |
| 5,650,214 A | 7/1997 | Anderson et al. |
| 5,658,639 A | 8/1997 | Curro et al. |
| 5,674,216 A | 10/1997 | Buell |
| 5,691,035 A | 11/1997 | Chappell |
| 5,710,094 A | 1/1998 | Minami et al. |
| 5,723,087 A | 3/1998 | Chappell |
| 5,730,961 A | 3/1998 | Goudjil |
| 5,779,691 A | 7/1998 | Schmitt |
| 5,891,544 A | 4/1999 | Chappell |
| 5,916,661 A | 6/1999 | Benson et al. |
| 5,916,663 A | 6/1999 | Chappell |
| 5,929,026 A | 7/1999 | Childs et al. |
| 5,968,025 A | 10/1999 | Roe et al. |
| 6,027,483 A | 2/2000 | Chappell |
| 6,080,415 A | 6/2000 | Simon |
| 6,086,715 A | 7/2000 | McNeil |
| 6,092,002 A | 7/2000 | Kastman et al. |
| 6,258,308 B1 | 7/2001 | Brady et al. |
| 6,277,466 B1 | 8/2001 | McNeil et al. |
| 6,306,409 B1 | 10/2001 | Ogawa |
| 6,330,730 B1 | 12/2001 | Davies et al. |
| 6,368,444 B1 | 4/2002 | Jameson et al. |
| 6,383,431 B1 | 5/2002 | Dobrin et al. |
| 6,395,133 B1 | 5/2002 | McNeil |
| 6,476,289 B1 | 11/2002 | Buell |
| 6,596,669 B1 | 7/2003 | Maruyama et al. |
| 6,710,221 B1 | 3/2004 | Pierce et al. |
| 6,719,742 B1 | 4/2004 | McCormack et al. |
| 6,746,766 B2 | 6/2004 | Bond et al. |
| 6,780,270 B2 | 8/2004 | Andersson |
| 6,794,023 B1 | 9/2004 | Melik et al. |
| 6,811,643 B2 | 11/2004 | McAmish |
| 6,818,295 B2 | 11/2004 | Bond et al. |
| 6,821,612 B1 | 11/2004 | Melik et al. |
| 6,843,949 B2 | 1/2005 | Brady et al. |
| 6,846,172 B2 | 1/2005 | Vaughn et al. |
| 6,849,319 B2 | 2/2005 | Cree et al. |
| 6,861,571 B1 | 3/2005 | Roe et al. |
| 6,911,022 B2 | 6/2005 | Steger et al. |
| 6,946,506 B2 | 9/2005 | Bond et al. |
| 6,984,770 B2 | 1/2006 | Graeme, III et al. |
| 7,183,231 B2 | 2/2007 | Hoying et al. |
| 7,270,861 B2 | 9/2007 | Broering et al. |
| 7,306,582 B2 | 12/2007 | Adams et al. |
| 7,311,696 B2 | 12/2007 | Christon et al. |
| 7,388,123 B2 | 6/2008 | Cowell et al. |
| 7,402,157 B2 | 7/2008 | Christon et al. |
| 7,485,403 B2 | 2/2009 | Khan |
| 2002/0062115 A1 | 5/2002 | Wada et al. |
| 2003/0091803 A1 | 5/2003 | Bond et al. |
| 2003/0109605 A1 | 6/2003 | Bond et al. |
| 2003/0109839 A1 | 6/2003 | Costea et al. |
| 2004/0170813 A1 | 9/2004 | Digiacomantonio et al. |
| 2004/0265534 A1 | 12/2004 | Curro et al. |
| 2005/0021753 A1 | 1/2005 | Coleman |
| 2005/0064136 A1 | 3/2005 | Turner et al. |
| 2005/0123726 A1 | 6/2005 | Broering et al. |
| 2005/0170726 A1 | 8/2005 | Brunson et al. |
| 2005/0256479 A1 | 11/2005 | Carlucci et al. |
| 2006/0021536 A1 | 2/2006 | Song et al. |
| 2006/0025735 A1 | 2/2006 | Berg, Jr. et al. |
| 2006/0025736 A1 | 2/2006 | Berg, Jr. et al. |
| 2006/0025737 A1 | 2/2006 | Song et al. |
| 2006/0068168 A1 | 3/2006 | Olson et al. |
| 2006/0072429 A1 | 4/2006 | Nagai et al. |
| 2006/0087053 A1 | 4/2006 | ODonnell et al. |
| 2006/0089071 A1 | 4/2006 | Leidig et al. |
| 2006/0246802 A1 | 11/2006 | Hughes et al. |
| 2006/0286343 A1 | 12/2006 | Curro |
| 2007/0154687 A1 | 7/2007 | Luthi et al. |
| 2007/0156106 A1 | 7/2007 | Klofta et al. |
| 2008/0027405 A1 | 1/2008 | Laviz et al. |
| 2008/0091162 A1 | 4/2008 | Maldonado et al. |
| 2008/0132865 A1 | 6/2008 | Li et al. |
| 2008/0195072 A1 | 8/2008 | Warner |
| 2008/0206529 A1 | 8/2008 | Veminami et al. |
| 2008/0228157 A1 | 9/2008 | McKiernan et al. |
| 2008/0233379 A1 | 9/2008 | O'Connor |
| 2008/0234644 A1 | 9/2008 | Hansson et al. |
| 2008/0269704 A1 | 10/2008 | Hansson et al. |
| 2008/0277621 A1 | 11/2008 | MacDonald et al. |
| 2008/0279253 A1 | 11/2008 | MacDonald et al. |
| 2008/0287903 A1 | 11/2008 | Vega et al. |
| 2008/0305328 A1 | 12/2008 | Green et al. |
| 2009/0030390 A1 | 1/2009 | Hammons et al. |
| 2009/0058892 A1 | 3/2009 | Vandemark |
| 2009/0143516 A1 | 6/2009 | MacDonald et al. |
| 2009/0191476 A1 | 7/2009 | Rogers et al. |
| 2009/0191480 A1 | 7/2009 | Rogers et al. |
| 2009/0194218 A1 | 8/2009 | Torstensson et al. |

FOREIGN PATENT DOCUMENTS

| | | |
|---|---|---|
| JP | 2001123088 | 5/2001 |
| JP | 2002138322 | 5/2002 |
| JP | 2003/199791 A | 7/2003 |
| JP | 2007/050145 A | 3/2007 |
| WO | WO-2004057110 A1 | 7/2004 |
| WO | WO-2006/018640 | 2/2006 |
| WO | WO-2006/114600 A3 | 11/2006 |
| WO | WO-2007/001270 A1 | 1/2007 |
| WO | WO-2007/032710 A1 | 3/2007 |
| WO | WO-2007046073 A2 | 4/2007 |
| WO | WO-2007/067103 A1 | 6/2007 |
| WO | WO-2009/081385 A2 | 7/2009 |
| WO | WO-2009/093028 A2 | 7/2009 |
| WO | WO-2009/081385 A2 | 8/2009 |
| WO | WO-2009/112956 A2 | 9/2009 |
| WO | WO-2010/017353 A1 | 2/2010 |
| WO | WO-2010029328 A2 | 3/2010 |
| WO | WO-2011/025486 A1 | 3/2011 |
| WO | WO-2011056777 A1 | 5/2011 |

OTHER PUBLICATIONS

International Search Report dated Dec. 9, 2010, 7 pages.
U.S. Appl. No. 12/766,730, filed Apr. 23, 2010, Kelyn Anne Arora et al.
U.S. Appl. No. 12/766,698, filed Apr. 23, 2010, Kelyn Anne Arora et al.
U.S. Appl. No. 12/766,716, filed Apr. 23, 2010, Kelyn Anne Arora et al.
U.S. Appl. No. 12/611,962, filed Nov. 4, 2009, Kelyn Anne Arora et al.
U.S. Appl. No. 12/611,965, filed Nov. 4, 2009, Kelyn Anne Arora et al.
International Search Report dated Jun. 28, 2011, 5 pages.

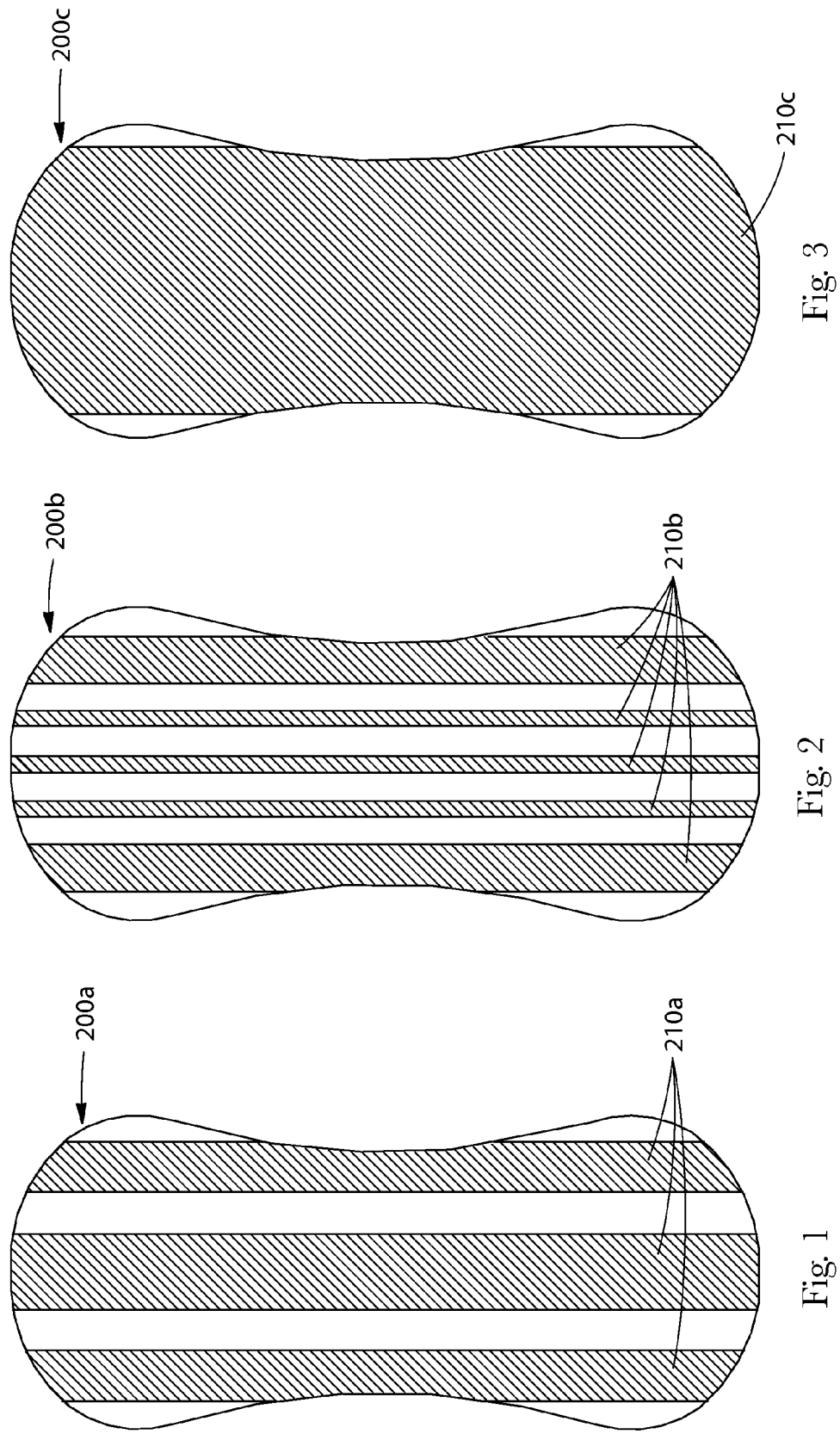

WEB SUBSTRATE HAVING ACTIVATED COLOR REGIONS IN TOPICAL ADDITIVE REGIONS

FIELD OF THE INVENTION

The present invention is related to activatable colorants that are activated to produce color. Specifically, the invention is related to web substrates comprising activatable colorants that are activated during application of topical additive producing activated color regions coinciding with regions where the topical additive is applied.

BACKGROUND OF THE INVENTION

A variety of absorbent articles that include different colored regions are available in the market. For instance, absorbent articles such as sanitary napkins and female adult incontinence articles that function to collect fluid discharged from a woman's vagina or urethra sometimes include colored regions to highlight various sections of the absorbent article. For instance the topsheet of the absorbent article may include topical additives such as lotions or hydrophilic coatings proximal the central portion of the absorbent article that are highlighted by color regions that differ in color from portions of the absorbent article remote from the central portion of the absorbent article. Such color regions can be made to highlight regions including the topical additives. For most applications, it is preferred that the topical additives such as lotions not include colorants that can transfer to a wearer's skin or clothing. As a result, the colored regions and topical additive regions are typically produced independent of one another requiring registration.

High speed manufacturing lines can include equipment and processing to apply topical additives such as lotions to web substrates during production of articles such as disposable absorbent articles. Such equipment can represent a significant capital cost to manufacturing. Adding printing capability to the manufacturing process in order to highlight the regions including topical additives represents an additional capital cost and complexity in order to register the printing with the regions including the topical additive. For manufacturers to effectively manage the cost, it is advantageous to use existing manufacturing lines to continue manufacturing absorbent articles. In some instances, the approach manufacturers have chosen to provide for colored regions might not be easily adapted to provide for colored regions that coincide with regions including lotion due to the crowded nature of the manufacturing line. Thus, if a manufacturer desires to provide for visual elements on regions of the absorbent article including topical additives, the manufacturer might have to retool the manufacturing line to provide for additional printing and registration capabilities, thus incurring significant additional capital cost.

With these limitations in mind, there is an unaddressed need for providing color change in the regions of a web substrate including topical additives that occurs simultaneously with application of the topical additive, thus eliminating the need for registration. In addition there is a need for web substrates having regions including topical additives such as lotion with colored regions that coincide with the topical additives regions that can be manufactured cost effectively using existing manufacturing capability. Still further there is a need for providing absorbent articles with colored regions coinciding with deformed regions and colored regions coinciding with topical additive regions without requiring additional printing or registration capabilities for registering the colored regions with the deformed regions and the topical additive regions.

SUMMARY OF THE INVENTION

Web substrates comprising activatable colorants and at least one topical additive region are disclosed where activated color regions are formed coinciding with the topical additive region. The activatable colorant can have both photoreactive and thermochromic material properties such that it first changes color to a first color upon exposure to electromagnetic radiation such as ultraviolet light and then changes to a second color upon exposure to heat. The heat can be associated with application of a topical additive during formation of the topical additive regions. The topical additives can include lotions, hot melt adhesives, coatings, and perfumes.

In one embodiment, the web substrate comprising an activatable colorant comprises a first activated color region produced in response to a first external stimulus comprising electromagnetic radiation. A plurality of topical additive regions are formed in the first activated color region. A plurality of second activated color regions are formed in the first activated color region in response to a second external stimulus comprising heat induced during formation of the topical additive regions. The plurality of second activated color regions are separated by the first activated color region and the second activated color regions coincide with the topical additive regions.

In another embodiment, the web substrate comprises an activatable colorant, a plurality of topical additive regions, and a plurality of deformed regions. The activatable colorant changes a first color in response to a first external stimulus comprising electromagnetic radiation producing a first activated color region. The activatable colorant in the first activated color region changes a second color in response to a second external stimulus comprising heat induced during application of a heated topical additive forming the topical additive regions. Second activated color regions are produced coinciding with the topical additive regions. The activatable colorant in the first activated color region also changes a third color in response to a third external stimulus comprising heat induced by strain during formation of deformed regions. Third activated color regions are produced coinciding with the deformed regions. The deformed regions are produced by mechanical deformation and can include out of plane deformed regions comprising ridges and grooves, rib-like elements, tufts and three dimensional cone shaped apertures. The deformed regions can also include two dimensional apertures and bond sites. For apertures, the third activated color regions circumscribe the apertures.

BRIEF DESCRIPTION OF THE DRAWINGS

These and other features, aspects and advantages of the present invention will become better understood with regard to the following description, appended claims, and accompanying drawings where:

FIG. 1 is a top view of an absorbent article including a topical additive according to the present invention.

FIG. 2 is a top view of an absorbent article including a topical additive according to the present invention.

FIG. 3 is a top view of an absorbent article including a topical additive according to the present invention.

DETAILED DESCRIPTION OF THE INVENTION

Definitions

Figure 4:
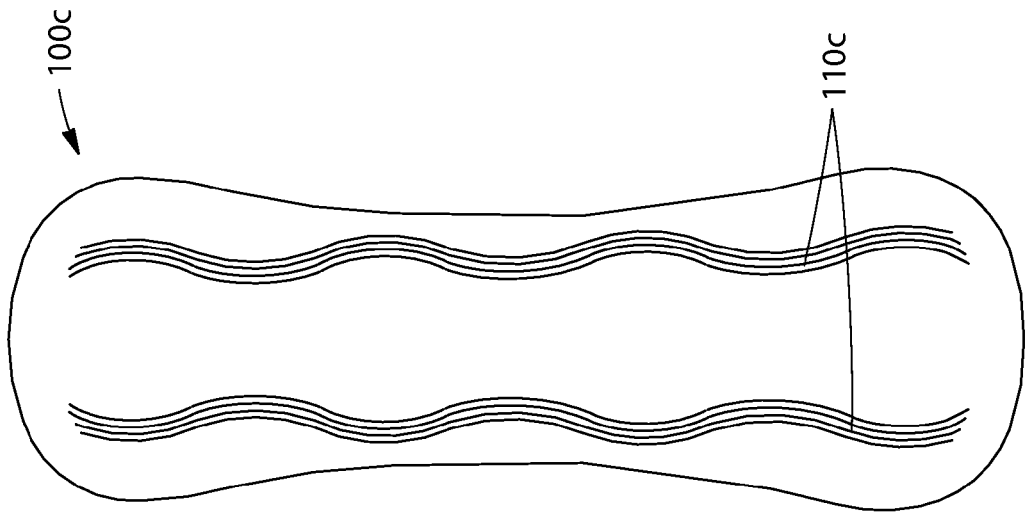
FIG. 4 is a top view of an absorbent article including a topical additive according to the present invention.

As used herein and in the claims, the term "comprising" is inclusive or open-ended and does not exclude additional unrecited elements, compositional components, or method steps.

As used herein, "machine direction" means the path that material, such as a web, follows through a manufacturing process.

As used herein "cross direction" means the path that is perpendicular to the machine direction in the plane of the web.

"Absorbent article" means devices that absorb and/or contain liquid. Wearable absorbent articles are absorbent articles placed against or in proximity to the body of the wearer to absorb and contain various exudates discharged from the body. Nonlimiting examples of wearable absorbent articles include diapers, pant-like or pull-on diapers, training pants, sanitary napkins, tampons, panty liners, incontinence devices, and the like. For the purpose of this invention, the term "absorbent article" not only includes the wearable portion of the article but also packaging for individual articles such as release paper wrappers (RPW) and applicators such as tampon applicators. Additional absorbent articles include wipes and cleaning products.

"Mechanical activation" is the mechanical deformation of one or more portions of an extensible material (e.g., film, nonwoven, fiber) that results in permanent elongation of the extensible material in the direction of activation in the X-Y plane of the material. Mechanical activation of a laminate that includes an elastic material joined to an extensible material typically results in one or more portions of the extensible material being at least partially permanently elongated, while the elastic material returns substantially to its original dimension. "Mechanically activated" means a material that has been subjected to an activation process. Suitable examples of absorbent articles, absorbent article components and processes for activation can be found in U.S. Pat. Nos. 5,156,793; 4,438,167; 5,202,173; 5,254,111; 5,296,184; 5,354,597; 6,258,308; 6,368,444; 6,811,643; 6,821,612; 6,843,949; and 6,794,023.

"Direction of mechanical activation" means the direction in which the material is stretched in the X-Y plane during the mechanical activation process. For laminates comprising elastic materials laminated to extensible nonwovens or films, the direction of mechanical activation is also the direction in which the laminate is capable of stretching after completion of the activation process. For materials that do not exhibit elastic behavior, the direction of mechanical activation refers to the direction of the dimension in the X-Y plane of the material that is increased most as a result of the mechanical activation process. Examples of directions of mechanical activation include the machine direction, the cross direction, the longitudinal direction, the lateral direction, and diagonal direction.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, airlaid, and bonded carded web processes, including carded thermal bonding. The basis weight of nonwoven fabrics is usually expressed in grams per square meter (g/m2). The basis weight of a laminate web is the combined basis weight of the constituent layers and any other added components. Fiber diameters are usually expressed in microns; fiber size can also be expressed in denier, which is a unit of weight per length of fiber. The basis weight of laminate webs suitable for use in the present invention can range from 6 g/m2 to 400 g/m2, depending on the ultimate use of the web. For use as a hand towel, for example, both a first web and a second web can be a nonwoven web having a basis weight of between 18 g/m2 and 500 g/m2.

As used herein, "spunbond fibers" refers to relatively small diameter fibers which are formed by extruding molten thermoplastic material as filaments from a plurality of fine, usually circular capillaries of a spinneret with the diameter of the extruded filaments then being rapidly reduced by an externally applied force. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky; to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer composition. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymer compositions extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross sectional area of the fiber and the various polymers are usually not continuous along the entire length of the fiber, instead usually forming fibers which start and end at random. Biconstituent fibers are sometimes also referred to as multi-constituent fibers.

As used herein, the term "non-round fibers" describes fibers having a non-round cross-section, and include "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET polyester).

"Laminate" means two or more materials that are bonded to one another by methods known in the art, e.g. adhesive bonding, thermal bonding, ultrasonic bonding, extrusion lamination.

As used herein, the term "tampon" refers to any type of absorbent structure such as, e.g., an absorbent mass, that can be inserted into the vaginal canal or other body cavity, such as, e.g., for the absorption of fluid therefrom, to aid in wound healing, and/or for the delivery of materials, such as moisture or active materials such as medicaments. In general, the term "tampon" is used to refer to a finished tampon after the compression and/or shaping process.

As used herein, the term "pledget" refers to an absorbent material prior to the compression and/or shaping of the material into a tampon. Pledgets are sometimes referred to as tampon blanks or softwinds.

As used herein, the term "applicator" refers to a device or implement that facilitates the insertion of a feminine hygiene product, such as, e.g., a tampon or pessary, into an external orifice of a mammal Suitable applicators include, e.g., telescoping, tube and plunger, and compact applicators.

The term "color" as referred to herein includes any primary color, i.e., white, black, red, blue, violet, orange, yellow, green, and indigo as well as any declination thereof or mixture thereof. The term 'non-color' or 'non-colored' refers to the color white which is further defined as those colors having an L* value of at least 90, an a* value equal to 0±2, and a b* value equal to 0±2.

"Color change" herein means that at least a part of layer including an activatable colorant changes its color in response to an external stimulus. The change in color is visible from outside the layer. A change in color "visible from outside the layer" as used herein means that the color change is detectable by the naked human eye.

"Activatable colorant" means a material which provides a color change in response to an external stimulus.

"External stimulus" means the exposure of the absorbent article to energy from outside the article in the form of pressure, temperature, electromagnetic radiation or combinations thereof.

"Activated color region" means areas containing a colorant that has been activated by external stimulus.

"Deformed region" means a region that has been strained sufficiently to produce distorted regions in the plane and/or out of the plane of the material.

"Visible" means those colors and wavelengths of light that are detectable by the human eye, nominally about 400-700 nanometers in wavelength.

"Electromagnetic radiation" means those areas of the spectrum amenable to industrial applications, such as the ultraviolet through the infrared wavelengths.

"Activatable chemistry" means those chemicals, monomers and polymers which are capable of being affected by an external stimulus.

"Disposable" means absorbent articles that are not intended to be launched or otherwise restored or reused as absorbent articles (i.e., they are intended to be discarded after a single use and, preferably to be recycled, composted or otherwise disposed of in an environmentally compatible manner).

The present invention provides web substrates containing activatable colorants that change color when exposed to external stimuli. The activatable colorant can produce a color change that is reversible or irreversible. However, preferably the activatable colorant according to the present invention produces a color change that is irreversible, thereby providing a permanent visual effect. Sources of activatable colorants include 'thermochromic', which means that the color change is induced by a change of temperature, or 'photoreactive', which means that the color change is induced by electromagnetic radiation, or 'piezochromic', which means that the color change is induced by pressure. Each of these sources of activatable colorants is discussed more fully below. The activatable colorant can also include pH sensitive dyes.

Web substrates can include a combination or blend of two or more activatable colorants where the activatable colorants are the same types but require different levels of external stimuli or different types requiring different types of external stimuli. For instance, for substrates including a blend of the same types of activatable colorants, the blend may include two different thermochromic colorants, whereas for substrates including a blend of different types of activatable colorants, the blend might include a thermochromic activatable colorant and a pH sensitive dye. Preferably the web substrate according to the present invention includes a single activatable colorant that is both photoreactive and thermochromic.

The web substrate according to the present invention can also include non activatable colorants. The non activatable colorant can include $TiO_2$ which is used to increase the opacity of the material. Non activatable colorant can also include a pigment. Pigments can be added to the substrate to provide an initial color which will affect the final color of activated color regions. For instance, a yellow pigment can be added to a substrate having an activatable colorant. If the activatable colorant ordinarily produces blue once activated, the yellow pigment will cause it to produce a green color once activated.

Once activated by an external stimulus, the activatable colorants form activated color regions in the substrate. The activated color regions can comprise uniform colored regions covering large sections or entire areas of the web substrate or nonunifom colored regions comprising varying patterns of colored regions. Alternatively, the activated color regions can include multiple color patterns, zone patterns and multiple shades of a single color. The activatable colorants can also be activated to form activated color regions comprising written text, graphics, and intricate artwork.

The web substrate according to the present invention preferably comprises an activatable colorant that changes to a first color when exposed to a first external stimulus producing a first activated color region and changes to a second color when the first activated color region is subsequently exposed to a second external stimulus producing a second activated color region. Depending on the type of activatable colorant, the first and second external stimuli can comprise heat (which includes heat induced by strain), pressure, electromagnetic radiation, and change in pH. As mentioned above the web substrate according to the present invention preferably comprises an activatable colorant that has both photoreactive and thermochromic properties. The activatable colorant is first activated by a first external stimulus comprising electromagnetic radiation such as ultraviolet light to produce a first activated color region. The first activated color region is subsequently activated by a second external stimulus comprising heat to produce a second activated color region within the first activated color region. The heat can be induced by strain; however, according to the present invention, the heat is preferably induced by application of a heated topical additive such as a hot melt adhesive, a lotion, or a coating such as a fabric conditioning composition.

In a preferred embodiment, the second activated color regions are limited to areas within the first activated color regions. In other words, areas outside the first activated color region that are exposed to the second external stimulus do not change color. For instance, in one embodiment, the first external stimulus comprising ultraviolet light can be exposed to the substrate in a particular pattern such that the first activated color region is limited to certain portions of the substrate. Only those portions forming the first activated color region that are exposed to the second external stimulus comprising heat will change color forming second activated color regions. Portions of the substrate exposed to heat that are outside of the first activated color regions do not change color and therefore, do not form the second activated color region.

As mentioned above, the second external stimulus preferably comprises heat induced by application of a topical additive such as a hot melt adhesive, lotion, or coating such as a fabric conditioning composition in the first activated color region. The topical additive forms a topical additive region in the substrate that changes the color of the substrate forming a second activated color region. The second activated color region coincides with the topical additive region. Preferably the topical additive region is formed in a first activated color region of the substrate such that the color of the substrate in the first activated color region is changed forming a second activated color region within the first activated color region. Since the color change induced by the topical additive occurs in the web substrate, the topical additive does not require a colorant. The topical additive is preferably translucent so that the second activated color region is visible through it and also so that the topical additive is not visible on a wearer's skin or stain a wearer's clothing once it transfers. Alternatively, in some applications the topical additive can be opaque so that the second activated color region is initially hidden by the topical additive and eventually appears once the topical additive is used up.

The topical additive according to the present invention can include an adhesive such as a hot melt adhesive. Once the hot melt adhesive is added to a web substrate, a topical additive region comprising the hot melt adhesive is formed. The heat from the hot melt adhesive can activate the colorant in the substrate producing an activated color region. For the present invention the topical additive region comprising the hot melt adhesive preferably overlaps a first activated color region so that a second activated color region is produced within the first activated color region. For this embodiment, the second activated color region can identify regions where hot melt adhesive is applied. In fact for applications requiring specific designs, the hot melt adhesive can be applied in patterns and the second activated color regions will coincide with the patterns.

Hot-melt adhesives used as construction adhesives in the manufacture of disposable absorbent articles typically include several components. These components include one or more polymers to provide cohesive strength, such as ethylene-vinyl acetate, copolymers, polypropylene, phenoxy resins, styrene-butadiene copolymers, ethylene-ethyl acrylate copolymers, low density polypropylenes, polyesters, polyamides, and polyurethanes. These polymers make up a significant part of the hot-melt adhesive composition. The composition also includes components such as, for example, a resin or analogous material (sometimes called a tackifier) to provide adhesive strength. Examples of such materials include hydrocarbons distilled from petroleum distillates, rosins and/or rosin esters, and terpenes derived, for example, from wood or citrus. The composition also typically includes waxes, plasticizers or other materials to modify viscosity. Examples of such materials include mineral oil, polybutene, paraffin oils, ester oils, and the like. Still further, the composition can optionally include additives, such as antioxidants or other stabilizers. A typical hot-melt adhesive composition might contain from about 15 to about 35 weight percent (wt. %) cohesive strength polymer(s); from about 50 to about 65 wt. % resin or other tackifier(s); from more than zero to about 30 wt. % plasticizer or other viscosity modifier; and optionally less than about 1 wt. % stabilizer or other additive.

FIGS. 1-3 illustrate examples of adhesive patterns used on a sanitary napkin absorbent article for personal hygiene. The embodiments shown include a panty liner 200*a-c* comprising adhesive patterns 210*a-c* used for securing the panty liner to the garments of a wearer. The adhesive patterns 210*a-c* can produce activated color regions coinciding with the adhesive patterns 210*a-c*.

In an alternate embodiment, the topical additive can include a lotion that is applied to a web substrate. Disposable absorbent articles, such as diapers, training pants, and catamenial devices having web substrates forming lotion topsheets are known. By applying a heated lotion to a topsheet including an activatable colorant according to the present invention where the colorant is first activated by electromagnetic radiation to form a first activated color region, second activated color regions are formed within the first activated color region that coincide with the topical additive regions comprising lotion. For this embodiment, the second activated color region identifies the areas where the lotion is present.

Lotions of various types are known to provide various skin benefits, such as prevention or treatment of diaper rash as disclosed in U.S. Pat. No. 6,861,571 issued to Roe, et al, U.S. Pat. No. 5,607,760 issued to Roe and U.S. Pat. No. 5,643,588 issued to Roe, et al. Such lotion compositions comprise (1) an emollient(s); (2) an immobilizing agent(s); (3) optionally a hydrophilic surfactant(s); and (4) other optional components. These lotions can be applied to the topsheet of absorbent articles, for example, and can be transferred to the skin of the wearer during use. For instance, when applied to the outer surface of a diaper topsheets, the lotion compositions can be transferable to the wearer's skin by normal contact, wearer motion, and/or body heat. Since the activatable colorant is in the web substrate rather than the lotion, the second activated color region is produced in the web substrate and not in the lotion. Therefore, the color does not rub off onto the wearer or transfer to the wearer with the lotion.

In preparing lotioned absorbent articles according to the present invention, the lotion composition including activatable colorant can be applied to the outer surface (i.e., body facing surface) of the topsheet, but can also be applied to the inner surface of the topsheet or to any other component of the absorbent article. Any of a variety of application methods that evenly distribute the lotion composition can be used. Suitable methods include spraying, printing (e.g., flexographic printing), coating (e.g., gravure coating), extrusion, or combinations of these application techniques, e.g. spraying the lotion composition on a rotating surface, such as a calender roll, that then transfers the composition to the outer surface of the topsheet. Lotion compositions of the present invention can be applied by printing methods, or continuous spray or extrusion as is known in the art, or as described in U.S. Pat. No. 5,968,025.

The lotion composition may be applied to the entire surface of the topsheet or portions thereof. The lotion composition can be applied in a stripe aligned with and centered on the longitudinal centerline of the disposable absorbent article. The lotion composition can be applied in a plurality of stripes having uniform or non-uniform widths. Alternatively the lotion can be aligned with and centered in opposition to the longitudinal centerline. It can be preferred that the lotion be applied in a plurality of stripes parallel to the longitudinal axis of the absorbent article. This allows for both transfer of the lotion to a broader area of the wearer.

Alternatively, the lotion composition can also be applied nonuniformly to the outer surface of the topsheet. By "nonuniformly" is meant that the amount, pattern of distribution, etc. of the lotion composition can vary over the topsheet surface. For example, some portions of the treated surface of the topsheet can have greater or lesser amounts of lotion composition, including portions of the surface that do not have any lotion composition on it. For example, the lotion composition can be applied on one region of the topsheet in the shape of a rectangle and/or a circle, and/or as multiplicity of dots.

Figure 5:
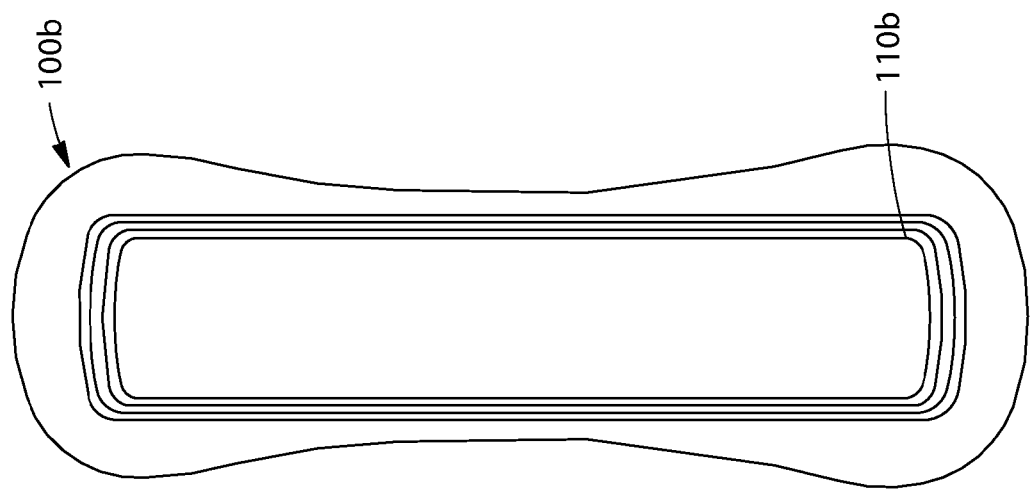
FIG. 5 is a top view of an absorbent article including a topical additive according to the present invention.
Figure 6:
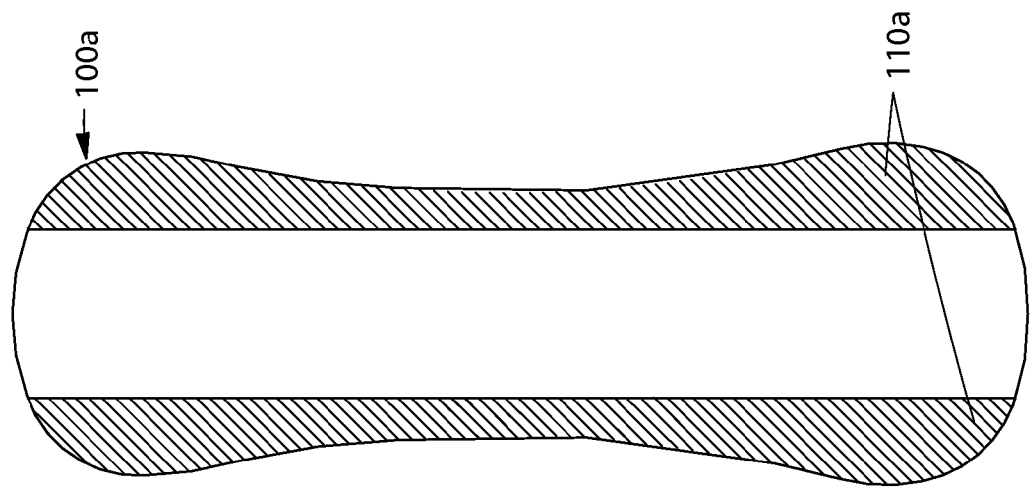
FIG. 6 is a top view of an absorbent article including a topical additive according to the present invention.

FIGS. 4 through 6 illustrate examples of lotion patterns used on a sanitary napkin absorbent article for personal hygiene. The embodiments shown include a panty liner 100a-c comprising lotion patterns 110a-c disposed on the skin facing surface of the panty liner 100a-c. The lotion patterns 110a-c can produce activated color regions coinciding with the lotion patterns 110a-c.

In an alternate embodiment, the topical additive can include a fabric conditioning composition that is applied to a web substrate. A fabric conditioning composition is typically used in dryer-activated fabrics as disclosed in U.S. Pat. No. 4,808,086 issued Feb. 28, 1989. Other applications for fabric conditioning compositions are disclosed in U.S. Pat. No. 5,094,761 and U.S. Pat. No. 5,929,026. For the present invention a web substrate comprising a dryer activated fabric can include an activatable colorant that is first activated by electromagnetic radiation such as UV light to produce a first activated color region. A fabric conditioning composition can be subsequently applied to the fabric producing topical additive regions within the first activated color region. The fabric conditioning composition is preferably applied at an elevated temperature sufficient to produce activated color regions within the topical additive regions identifying the presence of the fabric conditioning composition.

The web substrates according to the present invention can comprise films, nonwovens, air laids, fibers, filaments, particles and foams. The activatable colorant can be blended into or coated onto material forming the web substrate and can be disposed throughout or limited to only a portion of the web substrate where a color pattern is desired. The composition used to form the web substrates of the present invention, particularly films and nonwovens can include thermoplastic polymeric and non-thermoplastic polymeric materials. For fibers and nonwovens, thermoplastic polymeric material used in forming fibers must have rheological characteristics suitable for melt spinning. The molecular weight of the polymer must be sufficient to enable entanglement between polymer molecules and yet low enough to be melt spinnable. For melt spinning, thermoplastic polymers have molecular weights below about 1,000,000 g/mol, preferably from about 5,000 g/mol to about 750,000 g/mol, more preferably from about 10,000 g/mol to about 500,000 g/mol and even more preferably from about 50,000 g/mol to about 400,000 g/mol. Unless specified elsewhere, the molecular weight indicated is the number average molecular weight.

The thermoplastic polymeric materials are able to solidify relatively rapidly, preferably under extensional flow, and form a thermally stable fiber structure, as typically encountered in known processes such as a spin draw process for staple fibers or a spunbond continuous fiber process. Preferred polymeric materials include, but are not limited to, polypropylene and polypropylene copolymers, polyethylene and polyethylene copolymers, polyester and polyester copolymers, polyamide, polyimide, polylactic acid, polyhydroxyalkanoate, polyvinyl alcohol, ethylene vinyl alcohol, polyacrylates, and copolymers thereof and mixtures thereof. Other suitable polymeric materials include thermoplastic starch compositions as described in detail in U.S. publications 2003/0109605A1 and 2003/0091803. Other suitable polymeric materials include ethylene acrylic acid, polyolefin carboxylic acid copolymers, and combinations thereof. Other suitable polymeric materials comprising starch and polymers are described in U.S. Pat. Nos. 6,746,766, 6,818,295, and 6,946,506. Common thermoplastic polymer fiber grade materials are preferred, most notably polyester based resins, polypropylene based resins, polylactic acid based resin, polyhydroxyalkonoate based resin, and polyethylene based resin and combination thereof. Most preferred are polyester and polypropylene based resins.

Activatable Colorant

As briefly described above, activatable colorants can be 'photoreactive', which means that the color change is induced by electromagnetic radiation, 'thermochromic', which means that the color change is induced by a change of temperature, or 'piezochromic', which means that the color change is induced by pressure. These definitions comprise materials changing color irreversibly, reversibly or quasi-reversibly in response to the respective stimulus. The activatable colorants herein can either be coated onto a web substrate, such as on film or nonwoven, or can form an integral part of the substrate by being added e.g. to the polymeric master batch these components are made of. The activatable colorants herein change their color in response to external stimuli as defined hereinbefore.

c) Photoreactive Materials

Photoreactive materials change color in response to exposure to electromagnetic radiation. The color change can be irreversible providing a permanent change in color or it can be reversible providing a temporary change in color.

Photochromic materials are those that reversibly change color when exposed to light or changes in light intensity. Photochromic materials typically provide a reversible color change transiting from a colorless state to a color state upon exposure to light and back to a colorless state when reversed. Examples for photochromic materials are described in U.S. Pat. No. 6,306,409; U.S. Pat. No. 6,080,415 or U.S. Pat. No. 5,730,961.

Polychromic materials are those which are capable of generating multiple colors. Compounds based upon diacetylene, X—C≡C—C≡C—Y, when polymerized, are known to take on different color properties. Polymerization is typically achieved by exposure to certain types of radiation, such as ultraviolet radiation. Varying the intensity of the radiation causes differing degrees of polymerization, and different colors.

It is known that these properties can be utilized to achieve multi-color printing. See, for example; U.S. Pat. No. 4,705,742, "Processless Multicolour Imaging", issued on Nov. 10, 1987, assigned to Gaf Corporation; and WO2006/018640, "Multi-colour printing", published on Feb. 23, 2006, Sherwood Technologies Ltd. Both of these documents disclose methods of applying coatings comprising various diacetylene compounds to the surface of a substrate for the purpose of irradiating and forming an image on the surface of the substrate.

Particularly preferred materials are those that can be dispersed or blended into the polymeric matrix of the layers, such as those disclosed in PCT publication WO 2009/093028A2 and WO 2009/081385 A2, which are compounds which undergo a color change upon irradiation, and which have the general structure: X—C≡C—C≡C—Y—(CO)n-QZ wherein X is H, alkyl or —Y—(CO)n-QW; each Y is the same or a different divalent alkylene group; Q is O, S or NR; R is H or alkyl; W is H, alkyl or Z; each Z is the same or a different unsaturated alkyl group; and each n is 0 or 1.

Another example of a material of use in the present invention is a thermoplastic material comprising polymer mixed with a charge transfer agent and a photo acid generating agent such as those described in US 2009/0191476 A1. Exposure of the thermoplastic material comprising the charge transfer agent and photo acid generating agent to irradiation will bring about a color change reaction which can be used to create text, artwork, devices or other images and effects.

Web substrates according to the present invention preferably comprise photoreactive materials providing an irreversible, permanent change in color. Examples of photoreactive materials providing permanent color change are described in PCT publication WO 2009093028A2 which describes polychromic substances comprising diacetylene compounds that change color when subjected to irradiation. The type of radiation that performs the color change reaction with the diacetylene compounds includes laser or non-coherent, broadband or monochromatic radiation. Specific radiation types include ultraviolet, near, mid or far infrared, visible, microwave, gamma ray, x-ray or electron beam.

Ultraviolet irradiation is preferred for changing substrates comprising the diacetylene compounds from colorless or low visual color to color on exposure to ultraviolet irradiation, and then change to a color different to the first on subsequent exposure to infrared irradiation and/or heat. Heat can be applied directly, for example with heated tooling or the heat may be induced by strain during mechanical deformation of the web substrate. Methods for producing mechanical deformation are discussed more fully below. Methods of laser irradiation may be preferred for writing text and drawing intricate artwork directly on substrates comprising the diacetylene compounds, as laser imaging can be conveniently controlled by computer with the appropriate software and has superior resolution capability. However, similar effects can be obtained by passing radiation from, for example, an ultraviolet lamp through a mask before it reaches the substrates comprising the diacetylene compound.

Another application describing of photoreactive materials providing permanent color change includes WO 2009/081385 which describes thermoplastic material comprising polychromic substance wherein the polychromic substance is a functionalized diacetylene having a formula which has a general structure that is described therein.

Activation of photoreactive materials is preferably achieved using an ultraviolet lamp. One example is the Coil Clean (CC) Series ultraviolet fixtures available from American Ultraviolet (Lebanon, Ind.). Another UVC exposure unit suitable for use in activation of photoreactive materials consists of a metal enclosure containing 8 UV amalgam lamps and 8 ballasts with individual circuits for individual lamp controls and a fan for cooling lamps to maintain temperature. The lamps are 357 mm in length and are available from American Ultraviolet as part number GML750A.

Other examples of equipment that may be used for activation of photoreactive materials include the J3825 MonoCure Lamphead from Nordson UV Limited (Berkshire UK) and the 270S UV Lamp Assembly and Power Supply by Integrated Technology. The type of lamp within the unit may be changed to vary the spectral output as needed. Examples of relevant bulb types include "H", "V", "D" and "Q".

b) Thermochromic Materials

Thermochromic pigments are organic compounds that effectuate a reversible or irreversible color change when a specific temperature threshold is crossed. A thermochromic pigment may comprise three main components: (i) an electron donating coloring organic compound, (ii) an electron accepting compound and (iii) a solvent reaction medium determining the temperature for the coloring reaction to occur. One example of a commercially available, reversible thermochromic pigment is 'ChromaZone® Thermobatch Concentrates available from Thermographic Measurements Co. Ltd. Thermochromic pigments and the mechanism bringing about the temperature triggered color change are well-known in the art and are for example described in U.S. Pat. No. 4,826,550 and U.S. Pat. No. 5,197,958. Other examples of thermochromic pigments are described in published US application 2008/0234644A1.

Thermochromic or temperature sensitive color changing fibers are known from the textile field to be used in clothing, sport equipment, etc. The fibers are either produced by blending a thermochromic pigment in the base resin from which the fibers are to be produced, for example a polyolefin, such as polyethylene or polypropylene, polyester, polyvinyl alcohol etc. or by using a thermochromic coloring liquid for the fibers. The production of temperature sensitive color-changing fibers are disclosed in for example JP2002138322 and JP2001123088. The fibers change color at a selected temperature. The change of color is either reversible or irreversible.

An example of a fiber which can be used according to the invention is a thermochromic fiber which is partly characterized in that the flexural modulus of elasticity of a base resin is within the range of 300-1,500 MPa in the temperature-sensing color-changing fiber. The fiber is formed by melt blending a thermally color-changing pigment in a dispersed state in the base resin of a polyolefin resin and/or the polyolefin resin blended with a thermoplastic resin. The fiber is further described in JP 2002-138322.

Alternatively, the thermosensitive pigment may be of a microcapsule type which is known in the art of thermosensitive pigments.

c) Piezochromic Materials

Any piezochromic materials disclosed in the art are suitable herein as long as they meet the necessary health and safety requirements. An example is disclosed in U.S. Pat. No. 6,330,730.

In one example the piezochromic material is thermochromic and responds to a temperature increase caused by applied pressure. In another example the piezochromic material comprises a dye, which is encapsulated into microcapsules. Upon application of pressure these capsules break and release the dye, which then becomes visible. The color intensity is directly linked to the amount of pressure applied. Typical piezochromic materials require a pressure of from 14 to 140 kPa.

Most typically piezochromic activatable colorants change their color in an irreversible fashion after exertion of pressure. This is due to the fact that the color change was achieved by the destruction of microcapsules, in which the substances for achieving the color change were encapsulated.

Activation of the activatable colorant in the web substrate according to the present can be carried out in a variety of different ways. As previously discussed, the external stimuli activating the activatable colorant in the web substrate according to the present invention includes a first external stimulus comprising electromagnetic radiation that is sequentially followed by a second external stimulus comprising heat. The preferred source of electromagnetic radiation is ultraviolet light and the preferred source of heat is that induced application of a heated topical additive. For example, a web substrate can be unwound from a supply roll and exposed to an external stimulus comprising electromagnetic radiation such as ultraviolet light to induce color change and form a first activated color region. A heated topical additive can be subsequently applied to the web substrate in regions within the first activated color region producing second activated color regions within the first activated color regions.

In an alternate embodiment, a third external stimulus can be applied to the web substrate comprising heat induced by strain forming a third activated color region within the first activated color region. The strain is preferably caused by mechanical deformation during formation of a deformed region within the first activated color region. Preferably, the third activated color region coincides with the deformed region. For the present invention, the second and third activated color regions can overlap.

The deformed regions can include apertures or bonded regions formed in the x-y plane of the web but preferably include elements protruding in a z direction out of the x-y plane of the web such as ridges and grooves, rib-like elements and tufts. Bonded regions can be produced via thermal bonding, calendaring, ultrasonic bonding and CPW bonding. Apertures can be formed by a mechanical deformation processes such as rotary knife aperturing. Protruding elements can be formed via mechanical deformation processes including, but not limited to, ring rolling, SELF'ing, micro-SELF, and embossing. Mechanical deformation processes are discussed more fully below.

The heat induced by strain during formation of the deformed regions can result in third activated color regions exhibiting a color gradient which is proportional to the degree of deformation. The color gradient can be produced as a result of variable heat produced corresponding to variable strain during formation of the deformed regions. For instance, for three dimensional deformed regions comprising tufts formed via micro-SELF, the tufts can comprise a color gradient where the base and tip experience minimal color change since these regions experience little, if any, deformation and corresponding strain during formation of the tufts whereas the sides of the tuft experience heavy strain and corresponding heat resulting in major color change, Mechanical Deformation Processes Mechanical deformation processes use deformation members comprising counter rotating rolls, intermeshing belts or intermeshing two dimensional plates. The deformation members can be at ambient temperature or heated to an elevated temperature above ambient.

Figure 7:
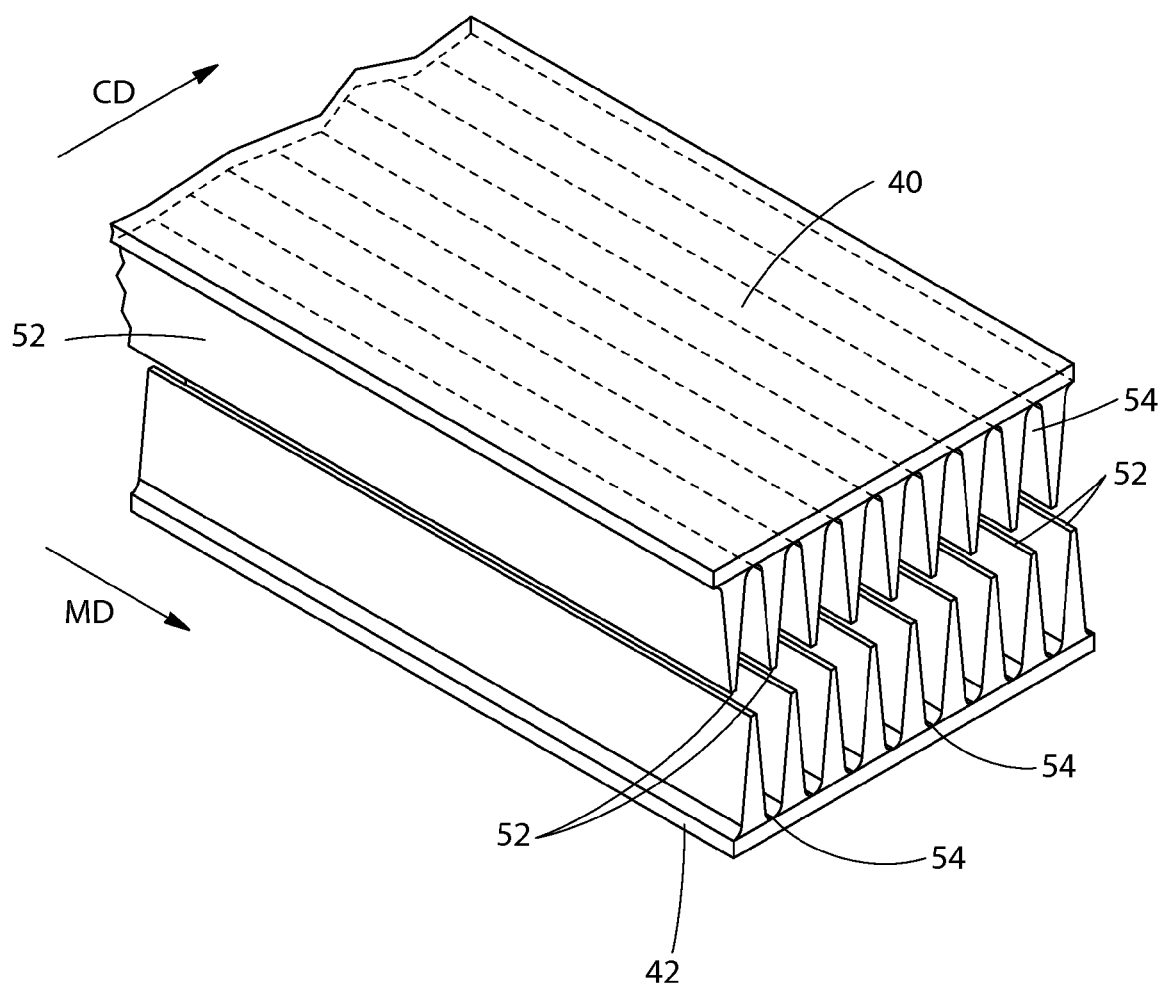
FIG. 7 is a perspective view showing portions of deformation members according to the present invention showing teeth and grooves arranged in a machine direction for incrementally stretching a web in the cross machine direction.
Figure 8:
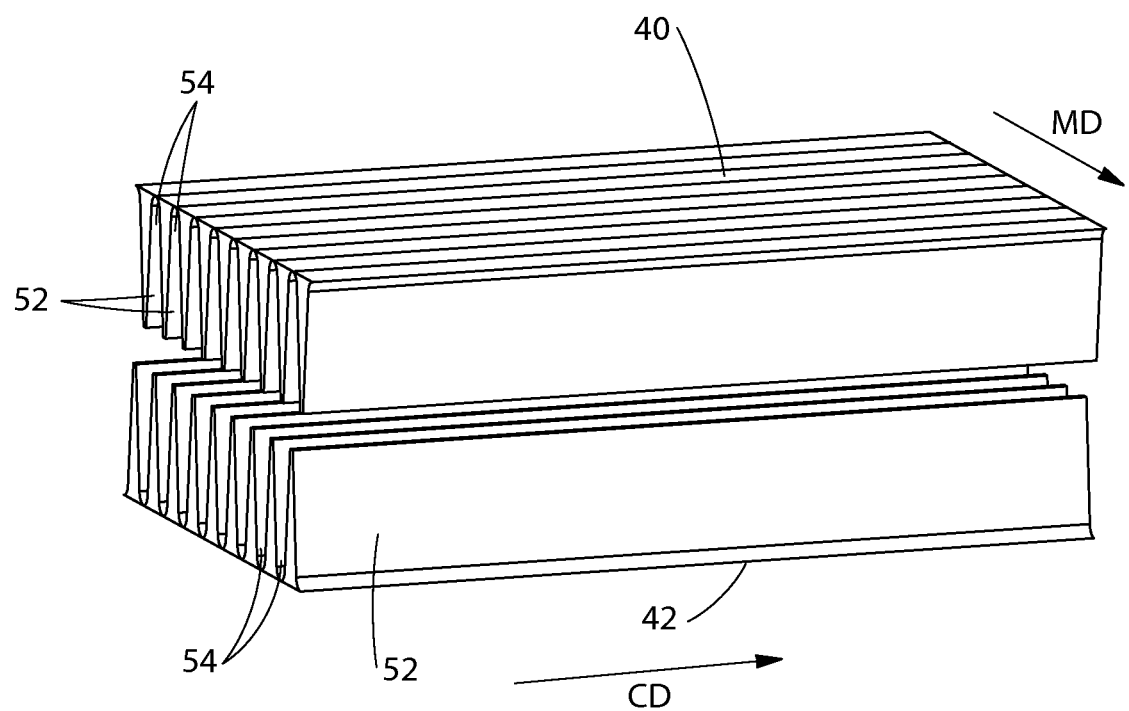
FIG. 8 is a perspective view showing portions of deformation members according to the present invention showing teeth and grooves arranged in a cross machine direction for incrementally stretching a web in the machine direction.

One mechanical deformation process which can be used to produce deformed regions and corresponding heat induced by strain in a web substrate is a process commonly referred to as ring rolling where intermeshing teeth and grooves of deformation members engage and stretch the web interposed therebetween. For ring rolling, the deformation members can be arranged to stretch the web in the cross machine direction or the machine direction depending on the orientation of the teeth and grooves. For instance, for incremental stretching in the cross machine direction CD as shown in FIG. 7, teeth 52 and grooves 54 on each deformation member 40, 42 are oriented in the machine direction MD. Conversely, for incremental stretching in the machine direction MD as shown in FIG. 8, the teeth 52 and grooves 54 on each deformation member 40, 42 are oriented in the cross machine direction CD. Deformation members comprising such cross machine direction teeth and grooves are kept in phase in the machine direction with respect to the intermeshing pattern.

Figure 9:
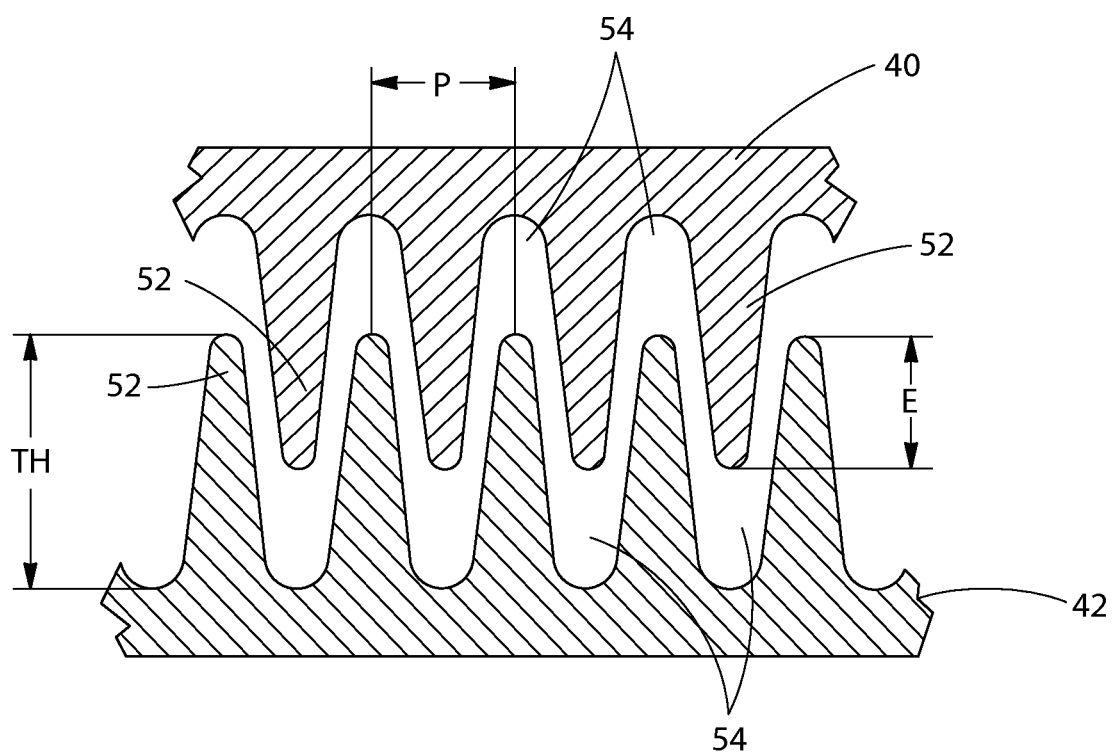
FIG. 9 is an enlarged, fragmentary, cross-sectional view showing the interengagement of teeth and grooves of deformation members as shown in FIG. 7 and FIG. 8.

FIG. 9 is an enlarged, fragmentary, cross-sectional view showing the interengagement of teeth 52 and grooves 54 of respective opposing deformation members 40, 42 in a deformation zone which stretch the web. Teeth 52 have a tooth height TH and are spaced apart from one another by a preferably uniform distance to define a tooth pitch P. As shown, teeth 52 of deformation member 40 extend partially into grooves 54 of the opposed deformation member 42 to define a "depth of engagement", E, as shown in FIG. 9. During deformation, the depth of engagement is controlled to gradually increase over at least a portion of the deformation zone.

Figure 10:
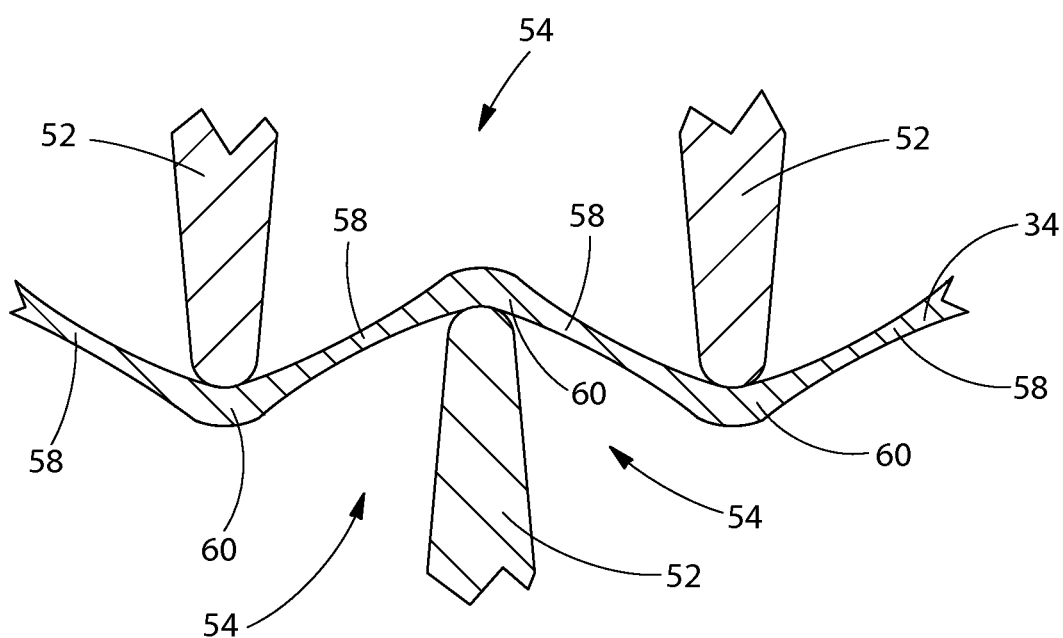
FIG. 10 is an even further enlarged view of the deformation members shown in FIG. 7 and FIG. 8 showing several interengaged teeth and grooves with a web of material therebetween.

FIG. 10 is an even further enlarged view of several interengaged teeth 52 and grooves 54 in the deformation zone with a web 34 of material therebetween. As shown, a portion of a web 34, which can be nonwoven web, is received between the interengaged teeth and grooves in the deformation zone. The interengagement of the teeth and grooves causes laterally spaced portions of web 34 to be pressed by teeth 52 into opposed grooves 54. In the course of passing between deformation members, the forces of teeth 52 pressing web 34 into opposed grooves 54 impose within web 34 tensile stresses that act in the machine or cross machine direction depending on the orientation of the teeth and grooves on the deformation members. The tensile stresses can cause intermediate web sections 58 that lie between and that span the spaces between the tips of adjacent teeth 52 to stretch or extend in a machine or cross machine direction, which can result in a localized reduction of the web thickness at each of intermediate web sections 58. For nonwoven webs, including air laid webs, the stretching can cause fiber reorientation, a reduction in basis weight, and controlled fiber destruction in the intermediate web sections 58.

Although the portions of web 34 that lie between the adjacent teeth are locally stretched, the portions of the web that are in contact with the tips of the teeth may not undergo a similar degree of extension. Because of the frictional forces that exist between the surfaces at the rounded outer ends of teeth 52 and the adjacent areas 60 of web 34 that are in contact with the tooth surfaces at the outer ends of the teeth, sliding movement of those portions of the web surfaces relative to the tooth surfaces at the outer ends of the teeth is minimized. Consequently, in some cases, the properties of the web 34 at those areas of the web that are in contact with the surfaces of the tooth tips change only slightly, as compared with the change in web properties that occur at intermediate web sections 58.

Teeth 52 can be generally triangular in cross section having generally rounded tooth tips, as shown in FIGS. 9 and 10. As shown teeth 52 have a tooth height TH (note that TH can also be applied to groove depth; in one embodiment tooth height and groove depth can be equal), and a tooth-to-tooth spacing referred to as the pitch P. The depth of engagement E, tooth height TH, and pitch P can be varied as desired depending on the properties of the webs being processed and the desired characteristics of the processed webs.

As will be appreciated by those skilled in the art, the sizes of the respective teeth and grooves can be varied within a wide range and would still be effective to carry out the present invention. In that regard, additional structural details of suitable deformation members according to the present invention are provided in U.S. Pat. No. 5,156,793, entitled "Method for Incrementally Stretching Zero Strain Stretch Laminate Sheet in a Non-Uniform Manner to Impart a Varying Degree of Elasticity Thereto," which issued on Oct. 20, 1992, to Kenneth B. Buell et al.; and in U.S. Pat. No. 5,167,897 entitled "Method for Incrementally Stretching a Zero Strain Stretch Laminate Sheet to Impart Elasticity Thereto," which issued on Dec. 1, 1992, to Gerald M. Weber et al. Other Activation patents include: U.S. Pat. No. 5,527,304, entitled "Absorbent Article with Elasticized Side Panels having Extension Panel," which issued on Jun. 18, 1996, to Buell; U.S. Pat. No. 5,674,216, entitled "Absorbent Article with Elasticized Side Panels," which issued on Oct. 7, 1997, to Buell; U.S. Pat. No. 6,476,289, entitled "Garment having Elastomeric Laminate," which issued on Jun. 18, 1996, to Buell; U.S. Pat. No. 5,628,741, entitled "Absorbent Article with Elastic Feature having a Prestrained Web Portion and Method for Forming Same," which issued on May 13, 1997, to Buell; U.S. Pat. No. 5,591,155, entitled "Disposable Training Pant having Improved Stretchable Side Panels," which issued on Jan. 7, 1997, to Nishikawa; U.S. Pat. No. 5,246,433, entitled "Elasticized Disposable Training Pant and Method of making the Same," which issued on Sep. 21, 1993, to Hasse; U.S. Pat. No. 5,464,401, entitled "Elasticized Disposable Training Pant having Differential Extensibility," which issued on Sep. 21, 1993, to Hasse; U.S. Pat. No. 5,575,783, entitled "Absorbent Article with Dynamic Elastic Feature Comprising Elasticized Hip Panels," which issued on Nov. 19, 1996, to Clear; U.S. Pat. No. 5,779,691, entitled "Fastening Tape for a Sanitary Article Particularly Disposable Diaper," which issued on Jul. 14, 1998, to Schmitt; U.S. Pat. No. 5,143,679, entitled "Method for Sequentially Stretching Zero Strain Stretch Laminate Web to Impart Elasticity thereto Without Rupturing the Web," which issued on Sep. 1, 1992, to Weber; U.S. Pat. No. 4,834,741, entitled "Diaper with Elastic Waist Band Elastic," which issued on May 30, 1989, to Sabee; and U.S. Pat. No. 4,968,313, entitled "Diaper with Elastic Waist Band Elastic," which issued on Nov. 6, 1989, to Sabee.

Another process for mechanically deforming a web which can produce the deformed regions and corresponding heat induced by strain of the present invention is a process commonly referred to as a "SELF" or "SELF'ing", where SELF stands for Structural Elastic Like Film. While the process was originally developed for deforming polymer film to have beneficial structural characteristics, it has been found that the SELF'ing process can be used to produce beneficial structures in nonwoven webs. Processes, apparatus, and patterns produced via SELF are illustrated and described in U.S. Pat. No. 5,518,801, entitled "Sheet Materials Exhibiting Elastic-Like Behavior," which issued on May 21, 1996, to Charles W. Chappell et al. Other patents issued to Chappell include U.S. Pat. No. 5,691,035 entitled "Web Materials Exhibiting Elastic-like Behavior," issued Nov. 25, 1997; U.S. Pat. No. 5,723,087 entitled "Web Materials Exhibiting Elastic-like Behavior," issued Mar. 3, 1998; U.S. Pat. No. 5,891,544 entitled "Web Materials Exhibiting Elastic-like Behavior" issued Apr. 6, 1999; U.S. Pat. No. 5,916,663 entitled "Web Materials Exhibiting Elastic-like Behavior," issued Jun. 29, 1999; and U.S. Pat. No. 6,027,483 entitled "Web Materials Exhibiting Elastic-like Behavior" issued Feb. 22, 2000.

Another process for mechanically deforming a web which can produce deformed regions and corresponding heat induced by strain of the present invention is a process that can best be described as "micro-SELF". Micro-SELF is a process that is similar in apparatus and method to that of the SELF process described above. The main difference between SELF and micro-SELF is the size and dimensions of the teeth on the toothed deformation member. The micro-SELF deformation member can be one of the deformation members forming the deformation zone in a preferred configuration having one patterned deformation member, e.g., micro-SELF deformation member, and one non-patterned grooved deformation member. However, in certain embodiments it may be preferable to use two micro-SELF deformation members having either the same or differing patterns, in the same or different corresponding regions of the respective deformation members. Such an apparatus can produce webs with deformed regions that, in nonwoven webs, can be described as tufts protruding from one or both sides of the processed web. The tufts can be closely spaced, but at least at their base can be spaced apart sufficiently to define void regions between tufts. A process using micro-SELF to form tufts in a web substrate is disclosed in co-pending, commonly owned patent applications US 2006/0286343A1, filed Jun. 17, 2005.

Another process for mechanically deforming a web which can produce deformed regions and corresponding second activated color regions according to the present invention is a process that can best be described as "rotary knife aperturing" (RKA). In RKA, a process and apparatus using intermeshing deformation members similar to that described above with respect to SELF or micro-SELF deformation members is utilized. The RKA process differs from SELF or micro-SELF in that the relatively flat, elongated teeth of a SELF or micro-SELF deformation member have been modified to be generally pointed at the distal end. Teeth, which are preferably heated, can be sharpened to cut through as well as deform a web to produce a three-dimensionally apertured web. In other respects such as tooth height, tooth spacing, pitch, depth of engagement, and other processing parameters, RKA and the RKA apparatus can be the same as described above with respect to SELF or micro-SELF. RKA teeth can have other shapes and profiles and the RKA process can be used to aperture fibrous webs, as disclosed in co-pending, commonly owned patent applications US 2005/0064136A1, filed Aug. 6, 2004, US 2006/0087053A1, filed Oct. 13, 2005, and US 2005/021753 filed Jun. 21, 2005.

Another process for mechanically deforming a web which can produce deformed regions comprising apertures according to the present invention is a process which uses a pin roll and a counter roll that rotate in opposite directions to form a nip through which the web substrate is fed as disclosed in U.S. Pat. No. 6,849,319. Pins protrude from the surface of the pin roll and holes are recessed into the counter roll. The pin roll and the counter roll are aligned so that pins of the pin roll mate with the holes of the counter roll. The pins may be heated. The method utilizing the pin roll and counter roll can be used to form apertured webs.

Another process for mechanically deforming a web substrate according to the present invention is embossing. Embossing of webs can provide improvements to the web such as increased bulk. During a typical embossing process, a web is fed through a nip formed between juxtaposed generally axially parallel rolls. Embossing elements on the rolls compress and/or deform the web. The embossed regions of the plies may produce an aesthetic pattern and provide a means for joining and maintaining the plies in face-to-face contacting relationship.

Embossing is typically performed by one of two processes; knob-to-knob embossing or nested embossing. Knob-to-knob embossing typically consists of generally axially parallel rolls juxtaposed to form a nip between the embossing elements on opposing rolls. Nested embossing typically consists of embossing elements of one roll meshed between the embossing elements of the other roll. Examples of knob-to-knob embossing and nested embossing are illustrated in the prior art by U.S. Pat. No. 3,414,459 issued Dec. 3, 1968 to Wells; U.S. Pat. No. 3,547,723 issued Dec. 15, 1970 to Gresham; U.S. Pat. No. 3,556,907 issued Jan. 19, 1971 to Nystrand; U.S. Pat. No. 3,708,366 issued Jan. 2, 1973 to Donnelly; U.S. Pat. No. 3,738,905 issued Jun. 12, 1973 to Thomas; U.S. Pat. No. 3,867,225 issued Feb. 18, 1975 to Nystrand; U.S. Pat. No. 4,483,728 issued Nov. 20, 1984 to Bauernfeind; U.S. Pat. No. 5,468,323 issued Nov. 21, 1995 to McNeil; U.S. Pat. No. 6,086,715 issued Jun. 11, 2000 to McNeil; U.S. Pat. No. 6,277,466 Aug. 21, 2001; U.S. Pat. No. 6,395,133 issued May 28, 2002 and U.S. Pat. No. 6,846,172 B2 issued to Vaughn et al. on Jan. 25, 2005.

Another process for mechanically deforming a web substrate according to the present invention is a method for selectively aperturing a nonwoven web which is disclosed in U.S. Pat. No. 5,658,639, U.S. Pat. No. 5,628,097, and U.S. Pat. No. 5,916,661. In this process a nonwoven web is weakened along a plurality of locations and then a tensioning force is applied causing the nonwoven web to rupture at the plurality of weakened locations creating a plurality of apertures in the nonwoven web coincident with the weakened locations. The web is weakened at a plurality of locations by passing it through a nip formed between a patterned calendar roll and an anvil roll. The patterned calendar roll has a plurality of protuberances that are disposed to precipitate a weakened, melt stabilized location in the web to affect a predetermined pattern of weakened, melt-stabilized locations in the nonwoven web. The tensioning force is subsequently applied to the web by passing it through an incremental stretching system comprising incremental stretching rollers referred to as ring rolls. The ring rolls, as described above under mechanical deformation processes, include a plurality of intermeshing teeth and grooves. Selectively apertured nonwoven webs including activatable colorant according to the present invention can include activated color regions in the weakened melt stabilized locations and the regions circumscribing the apertures as well as other areas of the web that are deformed as a result of the incremental stretching.

Each of the aforementioned deformation processes produce deformed regions comprising deformed elements (ridges and grooves, rib-like elements, apertures, tufts, embossments, etc.). The deformed regions can be produced uniformly throughout the web substrate or in individual zones. Depending on the equipment used, the size of each individual deformed element forming a deformed region can vary. For instance, each deformed element can have a length (or diameter) of less than 1.0 inch (2.54 cm), less than 0.5 inch (1.27 cm), less than 0.25 inch (0.635 cm) and less than 0.125 inch (0.318 cm). The number of deformed elements producing a deformed region and the size of the deformed region can also vary. For instance, the deformed regions can vary from an individual deformed element such as a single tuft, embossment, rib-like element or aperture to a plurality of deformed elements forming a deformed region where the size of the deformed region can range from 0.155 $in^2$ (1 $cm^2$) to 1550 $in^2$ (10,000 $cm^2$).

The web substrates having activatable colorants according to the present invention are applicable, but not limited to absorbent articles such as diapers, sanitary napkins, tampons, panty liners, incontinence devices, wipes and the like. For absorbent articles, the web substrates having activatable colorants can include topsheets, secondary topsheets, acquisition layers absorbent cores and backsheets. Alternatively, the web substrates can be applicable to various components of the absorbent article such as fasteners, barrier cuffs, and landing zones. In addition to absorbent articles, web substrates having activatable colorants according to the present invention are applicable to trash bags, packaging films and dryer sheets.

The color of the first activated colored region and second activated colored region in a web substrate can be measured by the reflectance spectrophotometer according to the colors L*, a*, and b* values. The L*, a*, and b* values are measured from the surface of a web substrate. The difference in color is calculated using the L*, a*, and b* values by the formula $\Delta E = [(L*X. - L*Y)2 + (a*X. - a*Y)2 + (b*X - b*Y)2]½$. Herein, the 'X' in the equation may represent the first activated colored region or the second activated colored region and 'Y' may represent the color of another region against which the color of such region is compared. X and Y should not be the same two points of measurement at the same time. In other words, for any particular comparison of the difference in color, the location of X does not equal (≠) the location of Y.

Where more than two colors are used, the 'X' and 'Y' values alternately include points of measurement in them also. The key to the ΔE calculation herein is that the 'X' and 'Y' values should not stem from the same measured point on the viewing surface. In those instances where there is effectively no non-colored portion within the confines of the measurement area, the 'X' values should flow from a point different in spatial relationship to the 'Y' values.

Reflectance color can be measured using the Hunter Lab LabScan XE reflectance spectrophotometer obtained from Hunter Associates Laboratory of Reston, Va. A web substrate is tested at an ambient temperature between 65° F. and 75° F. and a relative humidity between 50% and 80%.

The spectrophotometer is set to the CIELab color scale and with a D65 illumination. The Observer is set at 10° and the Mode is set at 45/0°. Area View is set to 0.125" and Port Size is set to 0.20" for films; Area View is set to 1.00" and Port Size is set to 1.20" for nonwovens and other materials. The spectrophotometer is calibrated prior to sample analysis utilizing the black and white reference tiles supplied from the vendor with the instrument. Calibration is done according to the manufacturer's instructions as set forth in LabScan XE User's Manual, Manual Version 1.1, August 2001, A60-1010-862. If cleaning is required of the reference tiles or samples, only tissues that do not contain embossing, lotion, or brighteners should be used (e.g., PUFFS tissue). Any sample point on the absorbent article containing the activated color to be analyzed can be selected.

The web substrate is placed over the sample port of the spectrophotometer with a white tile placed behind the web substrate. The web substrate is to be in a substantially flat condition and free of wrinkles.

The web substrate is removed and repositioned so that a minimum of six readings of color of the web substrate are conducted. If possible (e.g., the size of the activated color on the element in question does not limit the ability to have six discretely different, non-overlapping sample points), each of the readings is to be performed at a substantially different region on the externally visible surface so that no two sample points overlap. If the size of the activated colored region requires overlapping of sample points, only six samples should be taken with the sample points selected to minimize overlap between any two sample points. The readings are averaged to yield the reported L*, a*, and b* values for a specified color on an externally visible surface of an element.

In calculating the CIELab color space volume, V, maximum and minimum L*, a*, and b* values reported are determined for a particular set of regions to be measured. The maximum and minimum L*, a*, and b* values reported are used to calculate the CIELab color space volume, V according to the following formula:

$$V = \frac{4}{3}\left|\frac{\Delta L^*}{2}\right|\left|\frac{\Delta a^*}{2}\right|\left|\frac{\Delta b^*}{2}\right|$$

Within the above formula, ΔL* is the difference in L* values between the two colored regions being compared and is calculated by: ΔL*=L*X−L*Y. The Δa* is the difference in a* values between the two colored regions being compared and is calculated by: Δa*=a*X−a*Y. The Δb* is the difference in b* values between the two colored regions being compared and is calculated by: Δb*=b*X−b*Y. The CIELab color space volume can result in a solid substantially ellipsoidal in shape. If ΔL*, Δa*, and Δb* are equal, the solid will be spherical. As used herein, a "solid" refers to the mathematical concept of a three-dimensional figure having length, breadth, and height (or depth). An ellipsoidal volume is preferred to calculate volume because an ellipsoid generally requires the dimensional differences of ΔL*, Δa*, and Δb* to be relatively more uniform than other solids. Furthermore, it is believed that ellipsoidal volumes are more visually acceptable (i.e., less detectable color mismatch by human perception) than spherical volumes.

In some embodiments, the activated colors of at least two externally visible surfaces of discrete elements will occupy a CIELab color space volume of less than about 200. The externally visible surfaces are analyzed according to the Test Method described above. Upon analysis, the inherent color of an element comprising an externally visible surface will yield L*, a*, and b* coordinates. The CIELab color space volume is then calculated using the formula presented above. The resulting volume can be less than about 200. The resulting volume can be less than about 50.

It should be recognized that the activated colors of more than two discrete colored regions may occupy the aforementioned CIELab color space volumes. In calculating the CIELab color space volume for more than two elements, the CIELab color space volume is calculated using the maximum and minimum L*, a*, and b* from a set of elements. The maximum color values and minimum color values are used to calculate V according to the formula presented above.

Method of Color Measurement:

Each sample was laid flat and face down upon a Hewlett-Packard ScanJet 6300C scanner. The scanner lid was closed completely upon each sample and the sample was scanned. The resulting scanned sample images were saved under the "True Color" setting. Standards were measured the same way using the white and green Hunter tile numbers LX16566. The sample images were analyzed using Image J imaging and analysis software, ten locations within each distinct color region were sampled at random for each sample. Colors were measured in RGB color space. The RGB values were then mathematically transformed to XYZ and then to cieL*a*b* color space using the following algorithms:

Convert RGB to XYZ (Observer=2°, Illuminant=D65)

Reference: "A Standard Default Color Space for the Internet—sRGB" Michael Stokes (Hewlett-Packard), Matthew Anderson (Microsoft), Srinivasan Chandrasekar (Microsoft), Ricardo Motta (Hewlett-Packard) Version 1.10, Nov. 5, 1996 http://www.w3.org/Graphics/Color/sRGB 1. Convert from 8-bit RGB: Image J measures RGB in 8-bit. This step converts 8-bit to 0-1 scale for sRGB.

$var\_R=(R/255)$ //R from 0 to 255

$var\_G=(G/255)$ //G from 0 to 255

$var\_B=(B/255)$ //B from 0 to 255

2. Linearize RGB values to arrive at standard RGB (sRGB): RGB is a non-linear measurement. In order to linearize the expression in XYZ color-coordinate space this equation is employed.

if $(var\_R>0.04045)$ $var\_R=((var\_R+0.055)/1.055)^{2.4}$ else $var\_R=var\_R/12.92$ if $(var\_G>0.04045)$ $var\_G=((var\_G+0.055)/1.055)^{2.4}$ else $var\_G=var\_G/12.92$ if $(var\_B>0.04045)$ $var\_B=((var\_B+0.055)/1.055)^{2.4}$ else $var\_B=var\_B/12.92$ 3. Convert to 0-100 XYZ scale: XYZ is in a 0-100 scale. This converts to that scale.

$var\_R=var\_R*100$ $var\_G=var\_G*100$ $var\_B=var\_B*100$

4. Derived relationship for sRGB to XYZ tristimulus values: This is the multiplication array that describes the relationship between sRGB and XYZ when an object is illuminated with D65.

//Observer.=2°,Illuminant=D65

$X = \mathit{var\_R}*0.4124 + \mathit{var\_G}*0.3576 + \mathit{var\_B}*0.1805$ $Y = \mathit{var\_R}*0.2126 + \mathit{var\_G}*0.7152 + \mathit{var\_B}*0.0722$ $Z = \mathit{var\_R}*0.0193 + \mathit{var\_G}*0.1192 + \mathit{var\_B}*0.9505$ XYZ to cieL*a*b* (Observer=2°,Illuminant=D65)

Reference: ISO Standard 13655 International Organization for Standardization, ISO Geneva. "ISO 13655:1996 Graphic Technology-Spectral Measurement and Colorimetric Computation for Graphic Arts Images" (1996).

1. Defines slope in XYZ color coordinate space $\mathit{var\_X} = X/\mathit{ref\_X} \ //\mathit{ref\_X} = 95.047$ $\mathit{var\_Y} = Y/\mathit{ref\_Y} \ //\mathit{ref\_Y} = 100.000$ $\mathit{var\_Z} = Z/\mathit{ref\_Z} \ //\mathit{ref\_Z} = 108.883$ 2. Current ISO standard for converting between XYZ and L*a*b* if ($\mathit{var\_X} > 0.008856$) $\mathit{var\_X} = \mathit{var\_X}^{(1/3)}$ else $\mathit{var\_X} = (7.787 * \mathit{var\_X}) + (16/116)$ if ($\mathit{var\_Y} > 0.008856$) $\mathit{var\_Y} = \mathit{var\_Y}^{(1/3)}$ else $\mathit{var\_Y} = (7.787 * \mathit{var\_Y}) + (16/116)$ if ($\mathit{var\_Z} > 0.008856$) $\mathit{var\_Z} = \mathit{var\_Z}^{(1/3)}$ else $\mathit{var\_Z} = (7.787 * \mathit{var\_Z}) + (16/116)$ $CIE\text{-}L* = (116 * \mathit{var\_Y}) - 16$ $CIE\text{-}a* = 500 * (\mathit{var\_X} - \mathit{var\_Y})$ $CIE\text{-}b* = 200 * (\mathit{var\_Y} - \mathit{var\_Z})$ For each sample image, the delta L*, delta a*, and delta b* were calculated between the two distinct color regions using the following formula:

Delta $L* = L*$color 1 $- L*$color 2

Delta $a* = a*$color 1 $- a*$color 2

Delta $b* = b*$color 1 $- b*$color 2

Total color differences (delta E*) between the two distinct color regions for each sample were then calculated using the following formula:

Delta $E* = [(\text{Delta } L*)^2 + (\text{Delta } a*)^2 + (\text{Delta } b*)^2]^{1/2}$

EXAMPLES

The following non-limiting example is intended to illustrate potential embodiments of the present invention.

A spunbond nonwoven fabric was prepared comprising polypropylene and 2 weight percent Datalase Colour Change Pigment LT (from Datalase Ltd., Widnes, UK). Basis weight of the nonwoven is 18 grams per square meter. As made, the nonwoven is white. A handsheet of this nonwoven material was exposed to ultraviolet light through a quartz glass plate and a patterned cardboard stencil to produce a blue pattern of circles. This was done in a Chromato-Vue C-75 UV darkroom cabinet set to 254 nm with an exposure time of 90 seconds. The nonwoven was subsequently coated with a fabric conditioning composition at a temperature of 65-70° C. The white regions of the nonwoven material that had not been activated first by UV remained white, however the blue regions changed to pink. Color measurements and ΔE values are provided in Table 1.

Figure 11A:
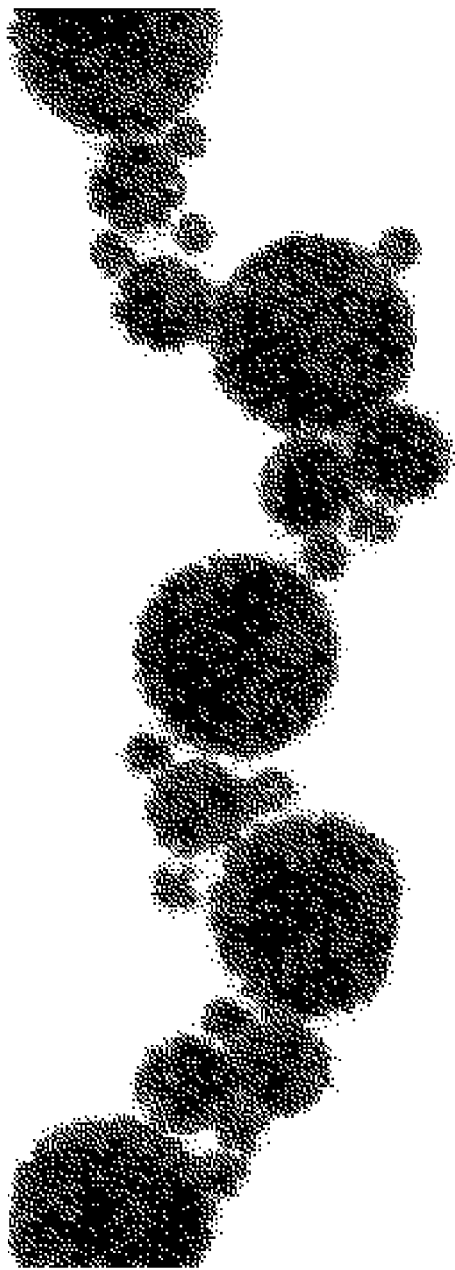
FIGS. 11a and 11b are plan views of a nonwoven web substrate including an activatable colorant according to the present invention where the web substrate was first exposed to ultraviolet light producing a pattern of dark circles as shown in FIG. 11a and subsequently exposed to a topical additive causing the pattern of dark circles to change color as shown in FIG. 11b.
Figure 11B:

A black and white photograph is provided in FIG. 11a and 11b. FIG. 11a shows the pattern of circles produced when the nonwoven was exposed to ultraviolet light. FIG. 11b shows the nonwoven after it was coated with a fabric conditioning composition. As shown, the white regions in FIG. 11a that had not been activated by UV light remained white, while the colored pattern of blue circles (shown as dark circles in the black and white photo) changed color to pink (shown as faded in the black and white photo).

TABLE 1

|  |  | Unactivated Regions | Activated Regions |
|---|---|---|---|
| Before Coating | L | 99.96 | 83.54 |
|  | a | −0.01 | 9.41 |
|  | b | −0.07 | −24.14 |
| After Coating | L | 99.94 | 83.39 |
|  | a | 0.03 | 19.74 |
|  | b | −0.10 | −11.67 |
|  | ΔE | 0.05 | 16.19 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or patent application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A web substrate having activated color regions and a topical additive region, wherein said web substrate comprises:
   (a) a first activated color region produced in response to a first external stimulus;
   (b) at least one second activated color region located within the first activated color region; and
   (c) a topical additive region that coincides with said second activated color region;

wherein said second activated color region is produced in response to a second external stimulus induced during formation of the topical additive region.

2. The web substrate according to claim 1 wherein the activated color regions are produced from activatable colorant having both photoreactive and thermochromic material properties.

3. The web substrate according to claim 1 wherein the first external stimulus comprises electromagnetic radiation.

4. The web substrate according to claim 1 wherein the second activated color region is formed in response to a second external stimulus comprising heat applied during formation of the at least one topical additive region.

5. The web substrate according to claim 1 wherein the web substrate is selected from the group comprising films, nonwovens, laminates, fibers, and foams.

6. The web substrate according to claim 1 wherein the topical additive is selected from the group comprising lotions, hot melt adhesives, coatings, and perfumes.

7. A web substrate having activated color regions and topical additive regions, wherein said web substrate comprises:
 (a) a first activated color region produced in response to a first external stimulus;
 (b) a plurality of second activated color regions located within the first activated color region; and
 (c) a plurality of topical additive regions that coincide with said second activated color regions;
wherein the plurality of second activated color regions are produced in response to a second external stimulus induced during formation of the topical additive regions.

8. The web substrate according to claim 7 wherein the activated color regions are produced from activatable colorant having both photoreactive and thermochromic material properties.

9. The web substrate according to claim 7 wherein the first external stimulus comprises electromagnetic radiation.

10. The web substrate according to claim 7 wherein the second external stimulus comprises heat.

11. The web substrate according to claim 7 wherein the web substrate comprises a thermoplastic material.

12. An absorbent article comprising a web substrate according to claim 7.

13. A web substrate having activated color regions, topical additive regions, and deformed regions, wherein said web substrate comprises:
 (a) a first activated color region having a first color produced in response to a first external stimulus;
 (b) a second activated color region located within the first activated color region;
 (c) topical additive regions that coincide with said second activated color region;
 (d) a third activated color region located within the first activated color region; and
 (e) deformed regions that coincide with said third activated color regions;
wherein:
 said second activated color region is produced in response to a second external stimulus induced during formation of the topical additive regions; and
 wherein said third activated color region is produced in response to a third external stimulus induced during formation of the deformed regions.

14. The web substrate according to claim 13 wherein the first external stimulus comprises electromagnetic radiation, the second external stimulus comprises heat induced by application of a topical additive during formation of the topical additive regions, and the third external stimulus comprises heat induced by strain during formation of the deformed regions.

15. The web substrate according to claim 13 wherein the second activated color regions overlap the third activated color regions.

16. The web substrate according to claim 13 wherein the second activated color regions coincide with the third activated color regions.

17. The web substrate according to claim 13 wherein the web substrate is selected from the group comprising films, nonwovens, laminates, fibers, and foams.

18. The web substrate according to claim 13 wherein the topical additive is selected from the group comprising lotions, hot melt adhesives, coatings, and perfumes.

19. The web substrate according to claim 13 wherein the deformed regions are selected from the group comprising ridges and grooves, tufts, and alternating rib-like elements.

20. The web substrate according to claim 13 wherein the deformed regions comprise apertures extending through the web substrate and the third activated color regions surround the perimeters of the apertures.

* * * * *